United States Patent [19]

DiMarchi

[11] Patent Number: 4,605,513

[45] Date of Patent: Aug. 12, 1986

[54] PROCESS FOR INHIBITING PEPTIDE CARBAMYLATION

[75] Inventor: Richard D. DiMarchi, Carmel, Ind.

[73] Assignee: Eli Lilly and Company, Indianapolis, Ind.

[21] Appl. No.: 638,848

[22] Filed: Aug. 8, 1984

[51] Int. Cl.$^4$ .............................................. C07K 7/40
[52] U.S. Cl. .................................................. 530/303
[58] Field of Search ................... 260/112.7, 112.5 R, 260/112.5 S

[56] References Cited

PUBLICATIONS

G. R. Stark, W. H. Stein, S. Moore (1960), *J. Biol. Chem.* 235, 3177–3181.
R. D. Cole (1961), *J. Biol. Chem.*, 236, 2670–2671.
G. R. Stark (1965), *Biochem.*, 4, 1030–1036.

*Primary Examiner*—Frederick E. Waddell
*Attorney, Agent, or Firm*—William C. Martens, Jr.

[57] ABSTRACT

There is disclosed herein a process for inhibiting carbamylation of peptides during treatment of said peptides, which comprises carrying out said treatment in the presence of a carbamylation-inhibiting amount of an agent selected from the group consisting of 1,2-ethylene diamine and 1,2-ethylene diamine-like materials.

14 Claims, No Drawings

PROCESS FOR INHIBITING PEPTIDE CARBAMYLATION

BACKGROUND OF THE INVENTION

It has been recognized for many years that cyanate readily reacts with certain amino acid side chain functional groups of a peptide [see G. R. Stark, *Method In Enzymology* 11, 590–594 (1967)]. While carbamylation is most rapid at sulfhydryl and imidazole sites, the resulting reaction products are of little concern due to their rapid reversal in slightly alkaline buffers. Modification of peptidyl primary amines (for example, NH$_2$-terminus and lysine residues) occurs at an appreciable rate and, for all practical purposes, is irreversible [see G. R. Stark, W. H. Stein, and S. Moore, *J. Biol. Chem.* 235, 3177–3181 (1960)]. At each site of primary amine carbamylation the peptide is reduced in physiological buffers one positive charge, thereby often resulting in diminished peptidyl solubility and/or biological activity. Since cyanate is an equilibrium product of aqueous urea solutions [see J. R. Marier and D. Rose, *Anal. Biochem.* 7, 304–314 (1964)], all peptides containing reactive functional groups, when handled in the presence of urea, are susceptible to irreversible carbamylation. Urea, being an excellent peptidyl solvent due to its ability to disaggregate structural order, facilitates carbamylation. These undesirable derivatized forms not only represent immediate losses in yield but also constitute complications in purification processes.

To diminish carbamylation of peptides, urea solutions are freshly freed of cyanate prior to use, and all chemical manipulations are conducted at reduced temperatures. The removal of cyanate by deionization or through pH reduction to below 2.0 is at best temporary, since ammonium cyanate reappears as an equlibrium product of aqueous urea. The low temperature operational restriction results in slower chemical reactions and reduced chromatographic performance. An excellent example of this problem can be seen in the production and purification of insulin. Insulin generally is purified at 4° C. in the presence of aqueous urea, usually 7M in concentration. Aqueous urea is well recognized as a reagent useful in inhibiting insulin polymerization and self-aggregation. However, carbamylated amino products are known to accumulate during purification even when using freshly deionized urea and low temperatures.

The discovery which forms the basis of the present invention resides in the use of a reagent from a class of reagents in the presence of the cyanate-containing or cyanate-generating medium. The properties of this reagent are ideally suited to scavenge cyanate under the customary peptide processing conditions before it can attack and carbamylate the product peptide.

SUMMARY OF THE INVENTION

Thus, this invention is directed to a process for inhibiting carbamylation of peptides during treatment of said peptides, which comprises carrying out said treatment in the presence of a carbamylation-inhibiting amount of an agent selected from the group consisting of 1,2-ethylene diamine and 1,2-ethylene diamine-like materials.

DETAILED DESCRIPTION OF THE INVENTION

Two alternatives which can be considered for diminishing losses due to carbamylation are addition of a protective scavenger and reversible amine protection. While the latter approach may permit complete protection it is not always desirable due primarily to the difficulty in achieving quantitative amine-specific derivatization and deprotection. If an appropriate reaction scavenger is available, its utilization is a more desirable and less expensive and demanding alternative to reversible protection. An ideal scavenger, of course, is one that is inexpensive and that provides complete protection from modification while otherwise being totally inert to all other reaction components. Since proteins contain a wide range and diversity of functional groups, each of which possesses a different reactivity toward a particular reagent, it is difficult a priori to predict an effective scavenger.

If an effective scavenger is to be found, it is important first to determine the optimum conditions for carbamylation. While it is well recognized that the unprotonated amine is one reactive entity in amine carbamylation, it is little appreciated whether cyanate (—OCN), its protonated conjugate acid (cyanic acid—HOCN), or both act as the second reactive entity [see, however, G. R. Stark, *Biochemistry* 4, 1030–1036 (1965)]. Different results are predicted for the relative rate of carbamylation of a peptidyl amino-terminus depending upon whether the reactive species is cyanate or cyanic acid. If cyanate is the reactive species, the rate of reaction should increase with increasing pH until a limit is reached at a pH slightly above the pKa of the amine. However, if cyanic acid is the reactive entity, the relative rate of reaction with an amine should be biphasic with a pH optimum of approximately 6.5. An investigation of the carbamylation of insulin A-chain S-sulfonate, a peptide possessing only one amine function (pKa of approximately 7.5), illustrates quite clearly that cyanic acid is the major entity that reacts with the unprotonated amine. Exposure of proinsulin (1α-amine, 2ε-amines) and insulin B-chain sulfonate (1α-amine, 1ε-amine) to freshly deionized urea at varying pH values revealed in both molecules the rapid appearance of a single modification as first observed in insulin A-chain sulfonate (1α-amine) with a pH optimum of approximately 7. Considerably later, the chromatographs exhibited evidence of further modification indicative of ε-amino modification. At pH 9, the respective appearance times for the α- and ε-amino carbamylation products were much closer; however, the total rate of modification was considerably slower than at pH 7. Presumably these effects are due to the reduced cyanic acid concentrations and the increased unprotonated ε-amine concentrations. Consequently, a reagent, inert to peptides and capable of forming irreversible complexes with cyanic acid at approximately pH 6.5±2.0, would be a highly attractive scavenger.

In seeking a suitable scavenger for cyanic acid, one might first be drawn to a mercaptan since mercaptans react rapidly with cyanic acid. However, they readily reverse at alkaline pH values, and thereby would provide only minimal protection. In addition, mercaptans are of no utility in the presence of proteins possessing disulfide bonds.

Amines are another possible cyanic acid scavenger. Of course, any useful amine must be one that is more reactive to cyanic acid than are the α- and ε-amines of peptides. The highly attractive scavengers for inhibiting peptide carbamylation by cyanic acid that form the basis of this invention are 1,2-ethylene diamine-like compounds and, in particular, 1,2-ethylene diamine itself. Apart from its ability to serve as a cyanic acid scavenger, 1,2-ethylene diamine is readily available, inexpensive, nearly inert to the structural integrity of the peptide being protected at the prescribe concentrations, and readily removable from the peptide mixture by lyophilization. More importantly, however, 1,2-ethylene diamine is highly suited as scavenger because its two amine functions are sterically unhindered and therefore possess no barrier to rapid reaction. Furthermore, the presence in 1,2-ethylene diamine of a potent electron withdrawing functionality [one of the two amine groups (1) $H_2NCH_2CH_2N^+H_3(2)$] two atoms removed from the amine of modification (amine 1) lowers the pKa of amine 1 to approximately 7.5, thereby providing ideal reactivity for peptide amino-terminus protection. The unprotonated amine (amine 1) of the scavenger, through intramolecular donation of electrons, increases the pKa of the other amine (amine 2) to approximately 10.7, thereby providing additional protection against carbamylation of any side-chain lysine $\epsilon$-amino groups present in the peptide. In comparison to their parent structure, 1,2-ethylene diamine-like compounds which possess substituents on one or both of the methylene carbons will exhibit an inhibited rate of reaction with cyanate, directly proportional to the steric size of the substituent. Modification of 1,2-ethylene diamine by mono- or di-substitution at one of the two amines will induce only a marginal alteration in effectiveness. Consequently, while other amines may provide some protection, within 1,2-ethylene diamine, a low molecular weight, water soluble reagent, a unique solution for optimum protection of both $\alpha$- and $\epsilon$-amino groups is achieved with no deleterious side effects.

As is evident throughout in the above, the essence of this invention resides in the use of 1,2-ethylene diamine or a 1,2-ethylene diamine-like compound. By the term "1,2-ethylene diamine-like" is meant a compound structurally related to 1,2-ethylene diamine and having cyanic acid scavenging properties similar thereto. Such compounds, apart from 1,2-ethylene diamine, are those having the formula

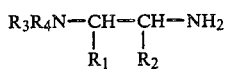

in which $R_1$, $R_2$, $R_3$, and $R_4$ are groups which, as a composite, do not exert significant changes (1) in the pKa values and (2) in the steric accessibility of the respective amino groups relative to the properties of 1,2-ethylene diamine itself.

A particular class of compounds for use in the process of this invention is that of the formula

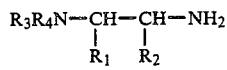

in which $R_1$ and $R_2$ independently are hydrogen, hydroxyl, $C_1-C_3$ straight chain alkyl, hydroxymethyl, or benzyl; and $R_3$ and $R_4$ independently are hydrogen, $C_1-C_3$ straight chain alkyl, hydroxymethyl, or benzyl.

Most preferred for use in the process of this invention is 1,2-ethylene diamine itself.

Other preferred compounds are those in which $R_1$ and/or $R_2$ is methyl, e.g., 1,2-diaminopropane and 2,3-diaminobutane; $R_1$ and/or $R_2$ is hydroxymethyl, e.g., 1-hydroxy-2,3-diaminopropane and 1,4-dihydroxy-2,3-diaminobutane; $R_1$ and/or $R_2$ is ethyl, e.g., 1,2-diaminobutane and 3,4-diaminohexane; $R_1$ and/or $R_2$ is n-propyl, e.g., 1,2-diaminopentane and 4,5-diaminooctane; $R_1$ and/or $R_2$ is hydroxyl, e.g., 1-hydroxy-1,2-diaminoethane and 1,2-dihydroxyl-1,2-diaminoethane; $R_1$ and/or $R_2$ is benzyl, e.g., 1,2-diamino-3-phenylpropane and 1,4-diphenyl-2,3-diaminobutane; $R_3$ and/or $R_4$ is methyl, e.g., N,N-dimethyl-1,2-diaminoethane, N-methyl-1,2-diaminoethane, and 1-(N-methyl)-1,2-diaminopropane; $R_3$ and/or $R_4$ is ethyl, e.g., N-ethyl-1,2-diaminoethane, N,N-diethyl-1,2-diaminoethane, and 2-(N-ethyl)-1,2-diaminopropane; $R_3$ and/or $R_4$ is n-propyl, e.g., N-n-propyl-1,2-diaminoethane, N,N-di-(n-propyl)-1,2-diaminoethane, and 1,1-di-(N-n-propyl)-1,2-diaminobutane; $R_3$ and/or $R_4$ is hydroxymethyl, e.g., N-hydroxymethyl-1,2-diaminoethane, N,N-di-(hydroxymethyl)-1,2-diaminoethane, and 2-(N-hydroxymethyl)-3-phenyl-1,2-diaminopropane; $R_3$ and/or $R_4$ is benzyl, e.g., N-benzyl-1,2-diaminoethane, 1,1-di-(N-benzyl)-1,2-diaminoethane; and 1-(N-benzyl)-1,2-diaminopropane; and the like.

The treatment of peptides as contemplated herein encompasses any of a wide range of peptide processing. Typical examples are purification, chemical modification, including, e.g., peptide sulfitolysis, and other such peptide processing steps. By and large, the most useful setting in which the process of this invention will find applicability is that in which peptides are subjected to treatment under conditions conducive to the generation and presence of cyanic acid. Much peptide treatment is carried out in the presence of urea, a recognizedly attractive peptidyl solvent but, unfortunately, one which also represents a major source of cyanic acid; therefore, the process of this invention finds great applicability in those peptide-treatment situations in which urea is present.

Generally, the scavenger used in the process of this invention is present at a concentration ranging from about 1 mM to about 200 mM, and preferably, from about 10 mM to about 50 mM, based upon the total processing medium.

Carbamylation inhibition is available for any peptide, irrespective of structure, when subjected to conditions in which small amounts of cyanic acid can be expected to be present. Thus, for example, peptides such as insulin A-chain, insulin B-chain, proinsulin, C-peptide, pancreatic polypeptide, growth hormone, growth hormone releasing factor, insulin-like growth factor, somatostatin, and, in particular, insulin which possesses two $\alpha$-amines, are candidates to which the process of the present invention can be applied.

The following example is provided for the purposes of illustrating the process of the present invention. It is not intended to be limiting upon the scope thereof.

EXAMPLE

Reagent grade urea was dissolved in distilled water to a concentration of 7M with no external heating. The solution was stored at 4° C. and deionized by passage through a 5×60 cm column of Amberlite ® MB-1 mixed bed ion-exchange resin. Technical grade 1,2-ethylene diamine (99% purity) was fractionally distilled, and a fraction boiling at 118±1° C. was collected and stored under nitrogen in a sealed amber bottle. Aqueous dilutions of 1,2-ethylene diamine were estimated by gas chromatographic analysis to be infinitely stable.

The rate of carbamylation in the presence of various scavengers was determined by examining the high performance reverse phase liquid chromatography (HPLC) profile of human proinsulin at various times of reaction in the temperature range of 4° C. to 35° C. Separation of the carbamylated proinsulins from the unmodified proinsulin was achieved at pH 8.1 on a Zorbax $C_8$ column (0.46×25 cm) using 0.1M $(NH_4)_2HPO_4$ buffer at 45° C. A linear gradient of acetonitrile from 25 to 30% v/v concentration eluted proinsulin preceded by its carbamylated derivatives in the order of tri-, di-, and mono-substituted proinsulin. Apart from the amino terminal carbamylated proinsulin which forms at the greatest rate and is unreactive to Edman sequence degradation, no specific identification of mono- or di-substituted derivatives was made. The tri-substituted form was identified indirectly by its slow rate of appearance and its inability to react with additional cyanate or with maleic anhydride. The disappearance of proinsulin was fitted to a least squares analysis for rate approximation.

The Table following illustrates several points regarding the carbamylation of human proinsulin ($\alpha$- and $\epsilon$-amino groups) in the presence of a variety of scavengers and at a range of concentrations. Although tris(hydroxymethyl)aminomethane (TRIS) possesses a pKa one unit below that of 2-ethanolamine, its ability to scavenge cyanic acid is substantially reduced, presumably due to steric interference. 1,2-Ethylene diamine provides significantly greater protection than the other scavengers. After 100 hours of treatment at 23° C. and 10 mM concentration, only about 7% of the human proinsulin was lost to carbamylation using 1,2-ethylene diamine as compared to about 41% and about 64% for 2-ethanolamine and TRIS, respectively. Increasing the concentration of 1,2-ethylene diamine to 100 mM resulted in negligible accumulation of carbamylated human proinsulin after two weeks at room temperature.

TABLE

Stability of Human Proinsulin (HPI) Using Various Scavengers
(7M urea, pH 7.5, 23° C., 500 μg HPI/ml)

| Scavenger | Concentration, mM | HPI remaining, % after Time, hours* | | | | | |
|---|---|---|---|---|---|---|---|
| | | 25 | 50 | 75 | 100 | 170 | 360 |
| TRIS | 10 | 92 | 73 | 49 | 36 | — | — |
| TRIS | 100 | 98 | 87 | 74 | 68 | — | — |
| HOEtNH$_2$ | 10 | 94 | 81 | 68 | 59 | — | — |
| HOEtNH$_2$ | 100 | 99 | 92 | 90 | 89 | — | — |
| H$_2$NEtNH$_2$ | 5 | 99 | 94 | 91 | 90 | 83 | 59 |
| H$_2$NEtNH$_2$ | 10 | 100 | 95 | 94 | 93 | 90 | 70 |
| H$_2$NEtNH$_2$ | 50 | 100 | 99 | 99 | 99 | 99 | 91 |
| H$_2$NEtNH$_2$ | 100 | 100 | 99 | 99 | 99 | 99 | 97 |

*Percentage of original HPI remaining unmodified.

As is apparent from the data provided in the Table, the use of 1,2-ethylene diamine at an appropriate concentration virtually eliminates carbamylation of peptidyl amines maintained at room temperature for extended periods. As a result, product losses can be virtually eliminated and chromatographic treatment simplified due to the near absence of carbamylated product and the ability to operate at room temperature.

I claim:

1. Process for inhibiting carbamylation of peptides in a cyanate-containing or cyanate-generating medium during treatment of said peptides, which comprises carrying out said treatment in the presence of a carbamylation-inhibiting amount of an agent selected from the group consisting of 1,2-ethylene diamine and 1,2-ethylene diamine-like materials.

2. Process of claim 1, in which such agent is a 1,2-ethylene diamine-like material having the formula

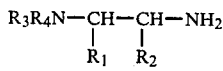

in which $R_1$, $R_2$, $R_3$, and $R_4$ are groups which, as a composite, do not exert significant changes (1) in the pKa values and (2) in the steric accessibility of the respective amino groups relative to the properties of 1,2-ethylene diamine itself.

3. Process of claim 1, in which such agent has the formula

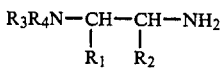

in which $R_1$ and $R_2$ independently are hydrogen, hydroxyl, $C_1$–$C_3$ straight chain alkyl, hydroxymethyl, or benzyl; and $R_3$ and $R_4$ independently are hydrogen, $C_1$–$C_3$ straight chain alkyl, hydroxymethyl, or benzyl.

4. Process of claim 3, in which such agent has the formula

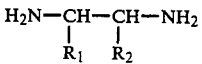

in which $R_1$ and $R_2$ independently are hydrogen, hydroxyl, $C_1$–$C_3$ straight chain alkyl, hydroxymethyl, or benzyl.

5. Process of claim 4, in which such agent has the formula

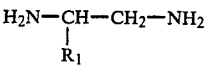

in which $R_1$ is hydrogen, hydroxyl, $C_1$–$C_3$ straight chain alkyl, hydroxymethyl, or benzyl.

6. Process of claim 3, in which such agent has the formula

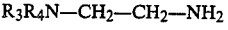

in which $R_3$ and $R_4$ independently are hydrogen, $C_1$–$C_3$ straight chain alkyl, hydroxymethyl, or benzyl.

7. Process of claim 6, in which such agent has the formula

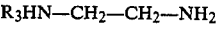

in which $R_3$ is hydrogen, $C_1$–$C_3$ straight chain alkyl, hydroxymethyl, or benzyl.

8. Process of claim 3, in which such agent is 1,2-ethylene diamine.

9. Process of claim 8, in which said peptides are subjected to a purification treatment.

10. Process of claim 9, in which said purification treatment is carried out in the presence of urea.

11. Process of claim 10, in which 1,2-ethylene diamine is present in a concentration of from about 1 mM to about 200 mM, based upon the peptide treatment medium.

12. Process of claim 11, in which 1,2-ethylene diamine is present in a concentration of from about 10 mM to about 50 mM, based upon the peptide treatment medium.

13. Process of claim 9, in which the peptide is insulin.

14. Process of claim 9, in which the peptide is proinsulin.

* * * * *